United States Patent [19]
Valentin

[11] 3,954,608
[45] May 4, 1976

[54] METHOD AND DEVICE FOR RAPID CHROMATOGRAPHIC SEPARATION

[75] Inventor: Patrick Valentin, Pont Eveque, France

[73] Assignee: Entreprise de Recherches et d'Activities Petrolieres ELF, Paris, France

[22] Filed: Aug. 13, 1974

[21] Appl. No.: 497,105

[30] Foreign Application Priority Data
Aug. 17, 1973 France ................................ 73.30063

[52] U.S. Cl. ................................ 210/24 C; 55/67; 55/197; 55/386; 210/198 C
[51] Int. Cl.² ...................................... B01D 15/08
[58] Field of Search .......... 210/31 C, 198 C, 21–23, 210/24 C; 55/67, 197, 386

[56] References Cited
UNITED STATES PATENTS

| | | |
|---|---|---|
| 1,818,702 | 8/1931 | Flowers .......................... 210/22 X |
| 2,023,109 | 12/1935 | Van Aidck ....................... 210/23 X |
| 2,720,980 | 10/1955 | Thomas .......................... 210/22 X |
| 3,728,256 | 4/1973 | Cooper ........................... 210/22 |
| 3,784,467 | 1/1974 | Tanimura et al ................. 210/31 C |

FOREIGN PATENTS OR APPLICATIONS
2,113,797  10/1972  Germany ............................ 210/21

Primary Examiner—John Adee
Attorney, Agent, or Firm—McNenny Farrington, Pearne & Gordon

[57] ABSTRACT

A method of rapid chromatographic separation by exchange of substances between two fluid phases circulating in coutercurrent flow, at least one phase being liquid, consists in injecting the substances to be separated into one of the phases, in causing the two phases to circulate on each side of a porous body having a thickness within the range of 1 to 200 microns while limiting the thickness of at least one liquid phase to a constant value within the range of 0.1 to 100 microns and in collecting after circulation the substances which have been separated in each of the two phases.

11 Claims, 3 Drawing Figures

METHOD AND DEVICE FOR RAPID CHROMATOGRAPHIC SEPARATION

This invention relates to a method of rapid chromatographic separation by exchange of substances between two fluid phases which circulate in countercurrent flow on each side of a porous material. The invention also relates to a device for carrying out the method.

As is already known, there are at present in existence two main types of methods of separation by exchange of substances between two mobile phases, one phase being intended to move relative to the other:

methods of the type involving distillation or gas-liquid or liquid-liquid countercurrent extraction and characterized by high productivity but fairly low selectivity, methods of the "chromatographic" type in which one of the active phases is fixed on a stationary support. Methods of this type are necessarily discontinuous and have low productivity but very high selectivity.

In conventional methods of chromatographic separation, namely methods involving separation of a substance between two phases in which at least one is a liquid or a gas, one of the two phases is stationary and the other is circulating; in these separations, saturation of the stationary phase retained by a solid phase makes it necessary to work in discontinuous operation in order to regenerate the stationary phase periodically and to recover from this latter the substances which have been fixed therein.

It is known that, in order to overcome the disadvantage attached to this discontinuous operation, consideration has been given to solutions whereby the phase which was previously stationary is made mobile by causing it to circulate countercurrent to the other phase. These solutions do not usually prove satisfactory since, in the event that the phase which is made non-stationary is a solid phase, compaction phenomena are created by inertia and these give rise to major problems in regard to industrial utilization. A second solution in which the non-stationary phase is also a fluid phase has consisted in making use of a packing column filled with Raschig rings, for example, as in the case of a distillation column. In this case, however, the thickness of the film in which the exchange of substance between the two phases takes place, that is to say the thickness of the so-called "active" phase in chormatography is typically of the order of one or several tens of microns.

The selectivity of a method of chromatographic separation, that is to say the capacity of this method for separating a substance is measured by the "height equivalent to a theoretical plate" (H.E.T.P.). This height is equal to the height (or to the length) of the exchanger divided by the number of theoretical plates provided. And this number of plates is proportional to the square of the quotient of the distance of retention, namely the distance traversed by the substance within the column, by the width at mid-height of the peak of the curve representing the concentration of the substance as a function of its position within the column. This "height equivalent to a theoretical plate" corresponding to a substance within a given phase depends to a considerable extent on the thickness of said phase as measured in the direction at right angles to the flow of said phase. As said thickness is greater, so the concentration gradients fall to zero at a lower rate across the thickness in respect of an equal rate of flow; in other words, as the variations in concentration are greater, so the dispersion of the concentration of the substance is more appreciable at the outlet of the column and so the height equivalent to a theoretical plate increases. If it is desired to have a high degree of selectivity, it is thus necessary either to reduce to zero the concentration gradient which is transverse to the flow, that is to say to have a very low rate of circulation with respect to the velocities of equalization of the concentration within the thickness of the fluid layer or to have thicknesses of fluid layers which are small and of constant value. Moreover, if it is desired to obtain increased productivity, it is essential to ensure a substantial throughput or in other words an appreciable rate of circulation of the phases.

The present invention is directed to a method of rapid chromatogrpahic separation by exchange of substances between two fluid phases circulating in countercurrent flow, at least one phase being liquid, the separation of the substances between said two phases being distinguished by high selectivity in conjunction with high productivity, wherein said method essentially consists in injecting the substances to be separated into one of the phases, in causing the two phases to circulated on each side of a porous body having a thickness within the range of 1 to 200 microns while limiting the thickness of at least one liquid phase to a constant value within the range of 0.1 to 100 microns and in collecting after circulation the substances which are separated in each of the two phases.

The variation of concentration in one phase in the direction at right angles to the flow of said phase of one of the substances to be separated is limited to a pre-established value calculated as a function of the selectivity to be obtained, the H.E.T.P. being such as to vary in a substantially quadratic manner as a function of the thickness of the liquid layer. The selectivity is also a function of the rate of circulation of the phase considered.

The present invention has the advantages of the two types of method of separation of a substance between two phases described earlier, that is to say productivity and selectivity; there has in fact been formed a "support" such that mobility is imparted to the liquid phase which circulates in thin layers imprisoned between one or a number of porous supports and which performs the same function as the stationary phase in conventional chromatography. These porous supports which permit exchange of the substances separate the two separate chambers in which the two phases circulate. The two "active" phases are fluid phases, one of which is liquid; the method permits separation of substances between a liquid phase and a gas phase, and two liquid phases.

One of the important properties of the method according to the invention is to make it necessary for the circulating fluid phases to have constant thicknesses (in the directions at right angles to the flow velocity) at any point and at any moment; this is due to the fact that the fluid phases are directed through the porous membranes in which the exchanges of substances take place between the two phases located on each side of one of these membranes. The porous membranes have a double function in the method according to the invention, namely of separating the two phases while permitting exchanges of substances between these latter and establishing the thicknesses of said phases. In consequence and in respect of mean thicknesses of identical phases and equal throughputs, the method according to the invention is distinctly more effective than all the existing methods of contacting in which the thickness of fluid streams can be guaranteed only on an average since the variations of thickness in methods of prior art reduce the selectivity of separations.

The support is a porous material of very small thickness, the pore diameter being within the range of 10 A and 100 microns and the thickness of the materials being within the range of 1 to 200 microns. The shape of the support is chosen so that the phases can be circulated thereon in layers of small thickness, that is to say within the range of 0.1 $\mu$ and 100 $\mu$.

In accordance with the invention, at least one of the two phases is caused to flow in forced circulation by a pumping means such as mechanical pumps, force of gravity or capillary forces. The motion of the phases is maintained by these different means which create a pressure difference at the ends of the separating column. The porous material is inactive and can be of any type. The fibers described can be selected from the group consisting of organic polymers such as cellulose acetates, nitrocellulose or substances formed of polyamide. It is also possible to employ glass or porous sintered metals.

In accordance with the invention, one of the devices for carrying out the method is characterized in that the porous body is in the form of a cylinder which limits the two internal and external chambers respectively to the wall of said cylinder, a liqud or gaseous phase being circulated within each chamber thus defined. It is possible to employ a plurality of porous cylinders enclosed within a vessel in which one of the phases A circulates within said vessel on the outside of all the cylinders and circulates countercurrent to the second phase B within the interior of all the cylinders. The plurality of parallel porous cylinders within the interior of the vessel are supplied in parallel and on the same side with the phase B. The substances to be separated are introduced into one of the two phases.

It should be pointed out that a system which makes use of a similar configuration of porous cylinders has been employed for the desalination of sea water, the sea water being circulated within the cylinders and being filtered by the porous wall, only the non-saline water being capable of passing through said wall; this perfusion is facilitated by the osmotic pressure difference between the saline water and the pure water. The physical concept of the method according to the invention is different in that the porous walls are not employed for the purpose of filtering one of the two phases but for the purpose of limiting the value of the thickness of the two phases which circulate in countercurrent flow and exchange substances having different solubility or volatility in the two phases. Moreover, this system of the prior art has low efficiency since it can be demonstrated that the separation efficiency is limited to one theoretical plate.

In an alternative construction of the device for carrying out the method according to the invention, the porous body is in the form of a segment separating two chambers in which one phase circulates. The porous segments are stacked in parallel relation and thus continuously separate numbered chambers in which phase A circulates within the even-numbered chambers and phase B circulates countercurrentwise within the odd-numbered chambers, the two series of chambers being supplied in parallel, one with phase A and the other with phase B.

A better understanding of the invention will in any case be gained from the following description of one embodiment of the invention which is given by way of nonlimitative example, reference being made to the accompanying figures, in which.

As mentioned in the foregoing, the method of chromatography consists in rapidly circulating two fluid phases in contact with each other through a porous body so designed as to ensure that the geometry prevents these two phases from having excessive thicknesses and that said thicknesses vary along the column. The small value, the constancy of the thickness of the active phases and the rapidity of flow endow the method with both selectivity and high productivity.

Figure 1:
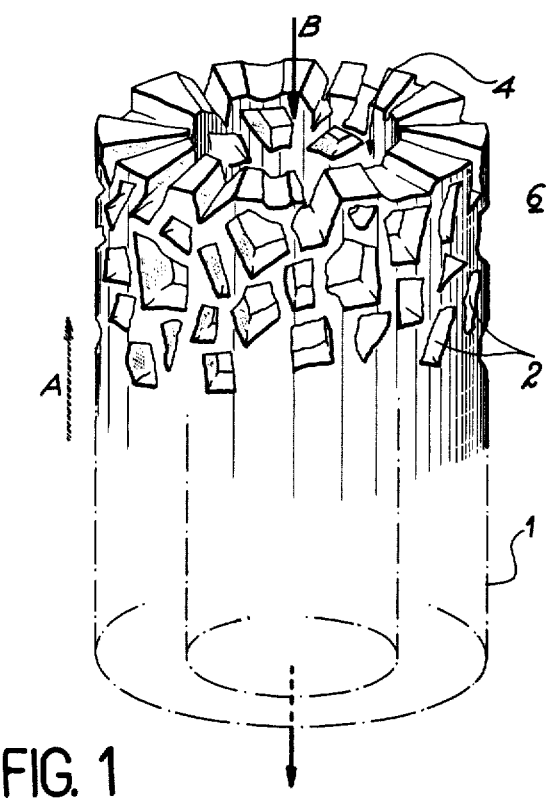
FIG. 1 is a diagram of a porous cylinder.

In FIG. 1, there is shown a cylinder of the porous body which has pores 2 and the surface of which separates two enclosed spaces or chambers 4 and 6, the phase A being circulated outside the cylinder and the phase B being circulated inside this latter.

Figure 2:
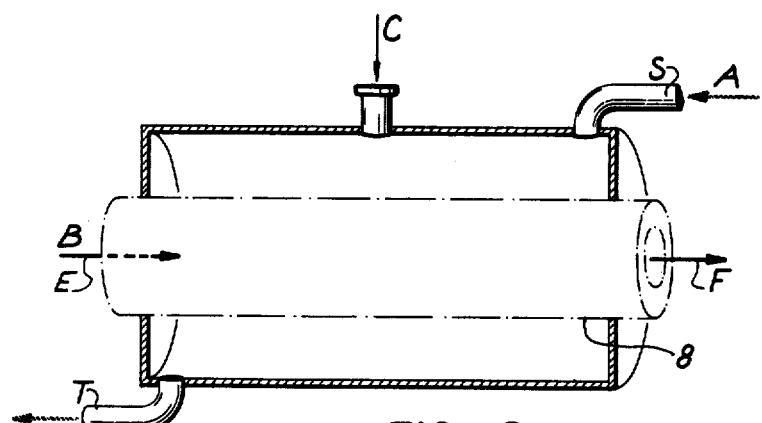
FIG. 2 is a diagram of construction of the selective separation device comprising a cylinder within a vessel.

In FIG. 2, there is a shown a vessel comprising a cylinder of the porous body. The phase A circulates within the vessel from S to T and the phase B circulates within the interior of the cylinder 8 from E to F. An inlet C serves to introduce the substances to be separated into the phase A.

Figure 3:
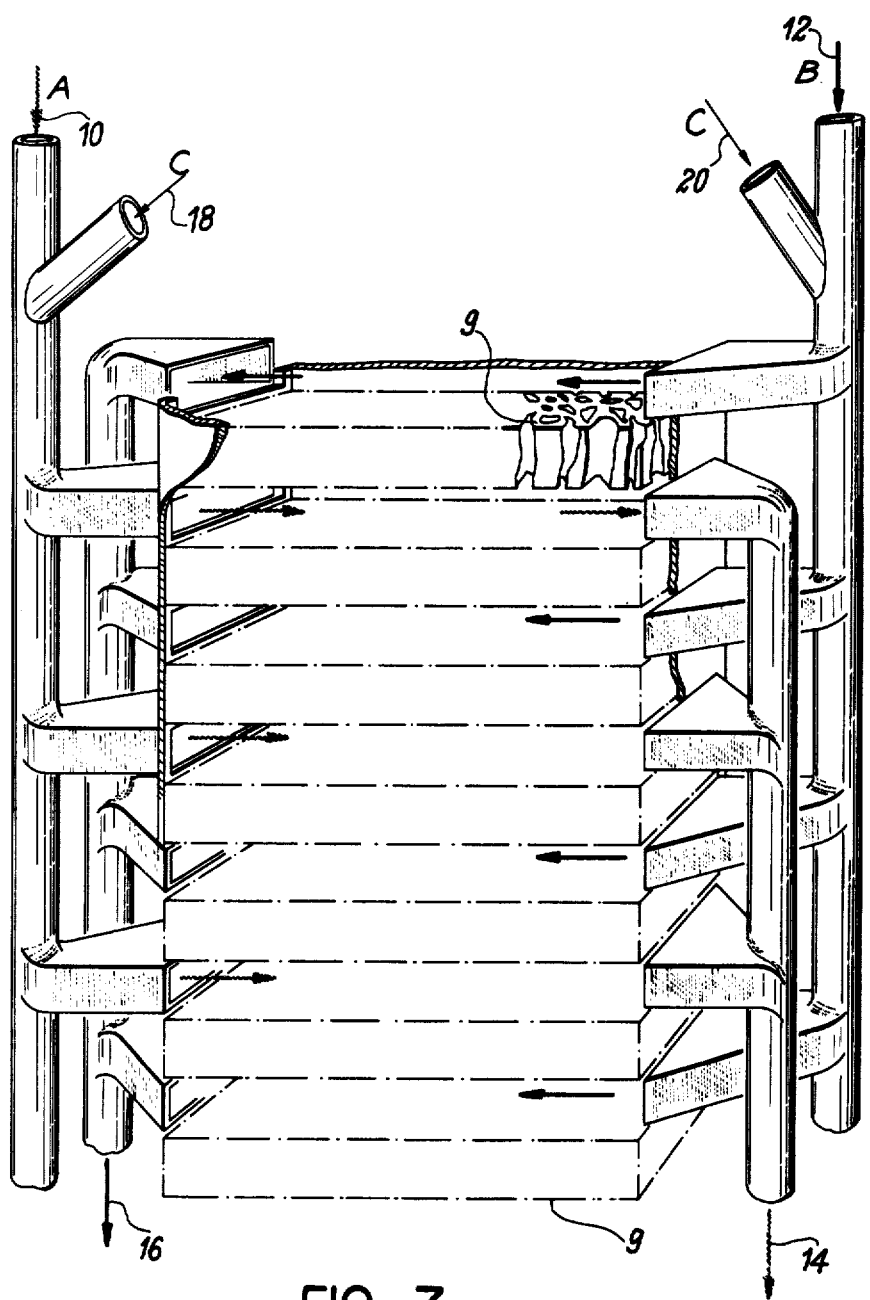
FIG. 3 is a diagram of construction of the separation device comprising a plurality of stacked porous segments.

In FIG. 3, there is shown a stack of parallel segments 9 which constitute a selective separator. The phase A is introduced at 10, the phase B at 12, the phase A circulates from 10 to 14, the phase B from 12 to 16, the substance C is introduced either at 18 or at 20.

The method which makes use of one of the two types of supports mentioned above can be employed either for purposes of analysis or for purposes of industrial separation.

In the event that the support has a cylindrical shape and that the two active phases which are present are a gas A and a liquid B, B circulates for example inside the cylinder A outside the cylinder in countercurrent flow; there are many different ways in which this device can be employed:

a. if it is desired to analyze a mixture of different constituents, a small quantity of the mixture is injected for a short instant into the gas A through the inlet C. There takes place a phenomenon of chromatographic separation between the constituents of the mixture which are more or less dissolved by the liquid B. It is possible to adjust the flow rate of B so that the constituents appear successively at the outlet F, the height equivalent to a theoretical plate being calculated so that the separation is greater than a predetermined value. This device is of considerable interest by virtue of the fact that the flow rates of A and B can readily be adjusted, with the result that readily separated components can be rapidly withdrawn and that the mixture together with products which cannot readily be separated are recycled within the interior of the vessel by reducing the flow rate of the liquid until their separation is achieved. It is also possible to employ a point located at C for the injection of the mixture of substances to be analyzed in order to ensure that the substances of the mixture are divided into two groups, namely the substances which are mainly delivered with the gas at T and the other substances which are mainly delivered in the liquid at F.

b. In the event that it is desired to separate industrially a mixture of two constituents G and H, a certain number of elementary cylinders each carrying a flow of liquid B are grouped together in parallel. These cylinders placed in side-by-side relation are in contact with a countercurrent flow of gas A which circulates within the vessel. At one point of the vessel, there is injected a continuous stream of the mixture which is to be separated and is constituted by the substances G and H. The flow rates of B and A are so adjusted that a liquid composed of B and G in the pure state is collected at the liquid-phase outlet and a compound of A and H in the pure state is collected at the gas-phase outlet.

The remarkable efficiency of the method is clearly brought out by the example of application in which two constituents are separated such that the ratio of volatilities to the phase $\beta$ is 1.001 (for example as in the case of isomers in which the boiling point differs by approximately 0.03°C).

To this end, there is employed a column having a diameter of 12 cm containing a closely arranged nest of juxtaposed porous cylinders having an external diameter of 60 microns and an internal diameter of 40 microns. The linear velocity of the liquid within the interior of the cylinders is 1 mm/sec and the linear velocity of the gases which flow outside the cylinders and in which the diffusion of substances is more rapid than within the liquids, is 10 cm/sec. By means of this device it is found possible to separate 14 g/hr of the 50—50 mixture of two insomers with a purity of 99% and a yield of 99%, which is wholly remarkable when taking into account the difficulty of the separation.

As the best mode of carrying out the invention, and for the chromatographic separation of two constituents like metaxylene and paraxylene the following parameters of the apparatus were used:

phase A: squalane (perhydrosqualene)
phase B: hydrogen
substance C, when introduced 66% of metaxylene 34% of paraxylene
mass of substance C introduced: 200 g per hour
atmospheric pressure
temperature 140°C (284°F)
fibers: porous cylinder of 200μ of external diameter and 100μ of internal diameter
124.000 fibers of 1 meter length
pore diameter around 500 A
linear velocity of the phases:
  gas (phase B) 20 cm/sec
  liquid (phase A) 2 cm/sec
Products obtained: 132 g/h of metaxylene, purity: 97%, at one end of the apparatus 68 g/h of paraxylene, purity 90%, at the other end
number of equivalent theoretical plates: 390.

This separation is not feasible by any other method using countercurrent flows and physical processes, as the ratio of volatilities is 1.015, a ratio closer to one than the ratio corresponding to heavy and normal water. To separate metaxylene from paraxylene it was formerly necessary to apply complicated chemical method (extraction with $HF/BF_3$ Japan Gas Chemical Process, Hydrocarbon processing Nov. 70 p. 133).

Two particularly advantageous methods of application of the method according to the invention are:
the separation of isotopes,
the separation of the dextrorotatory and levorotatory constituents of a racemic compound.

What we claim is:

1. A method of rapid chromatographic separation by exchange of substances between two fluid phases circulating in countercurrent flow, at least one phase being liquid, the separation of the substances between said two phases being distinguised by high selectivity together with high productivity, wherein said method comprises injecting the substances to be separated into one of the phases, causing the two phases to circulate on each side of a porous body having a thickness within the range of 1 to 200 microns while limiting the thickness of at least one liquid phase to a constant value within the range of 0.1 to 100 microns, and collecting after circulation the substances which have been separated in each of the two phases.

2. A method according to claim 1, wherein one phase is liquid and the other phase is gaseous, said liquid phase is perhydrosqualene and said gaseous phase is hydrogen, said substance to be separated consists essentially of metaxylene and paraxylene, and said separate substances collected after circulation are each at least 90% pure.

3. A method according to claim 2 wherein said substances to be separated are injected at the rate of 200 grams per hour, and said porous body is a porous cylinder of 200 microns external diameter and 100 microns internal diameter and 500 Angstrom pore diameter.

4. A method according to claim 1, wherein at least one of the two phases is caused to flow in forced circulation by a pumping means selected from the group of pumping means of the mechanical, gravity or capillary type.

5. A method according to claim 1, wherein the porous body is selected from the group constituted by the organic polymers, glass, porous sintered metals.

6. A method according to claim 1, wherein the size of the pores is within the range of 10 A to 100 microns.

7. A device for producing rapid chromatographic separation by exchange of substances between two fluid phases circulating in countercurrent flow comprising a porous body in the form of a cylinder having a wall which limits an internal and an external chamber to the wall of said cylinder, one of said phases being in said internal chamber, means to move said one phase in said internal chamber in a first direction parallel to said wall, the other of said phases being in said external chamber, means to move said other phase in said external chamber in a second direction parallel to said wall and opposite said first direction, the thickness of said porous body being within the range of 1 to 200 microns, and the thickness of each of said phases being within the range of 0.1 to 100 microns.

8. A device according to claim 7 including a vessel, a plurality of parallel porous cylinders within the interior of said vessel, means to supply the interior of each of said parallel porous cylinders with said one phase and the pore diameter of each of said parallel porous cylinders being within the range of 10 Angstroms to 100 microns.

9. A device according to claim 8 wherein said phases are perhydrosqualene and hydrogen, and said substances to be separated are metaxylene and paraxylene.

10. A device for producing rapid chromatographic separation by exchange of substances between two fluid phases circulating in countercurrent flow comprising a vessel having an interior, a first phase inlet manifold and a first phase outlet manifold communicating with said interior of said vessel, a second phase inlet manifold and a second phase outlet manifold communicating with said interior of said vessel, and a plurality of parallel flat porous bodies disposed within said interior of said vessel, said porous bodies being constructed and arranged to provide the sole means in said vessel to separate said first phase inlet and outlet manifolds from said second phase inlet and outlet manifolds, said porous bodies being further constructed and arranged to maintain open communication between said first phase inlet and outlet manifolds and between said second phase inlet and outlet manifolds, whereby said porous bodies define a plurality fo stacked parallel consecutively numbered chambers in which said first phase is within the even numbered chambers and said second phase is within the odd numbered chambers, means to circulate said first phase through said even numbered chambers from said first phase inlet manifold to said first phase outlet manifold in a first direction parallel to said porous bodies, means to circulate said second phase through said odd numbered chambers from said second phase inlet manifold to said second phase outlet manifold in a second direction parallel to said porous bodies and opposite said first direction, the thickness of each of said phases being a constant value within the range of 0.1 to 100 microns, and said porous bodies each having a thickness within the range of 1 to 200 microns.

11. A device according to claim 10, wherein said one phase is perhydrosqualene, said other phase is hydrogen, and said substances to be separated are metaxylene and paraxylene.

* * * * *